United States Patent [19]

Sohngen

[11] Patent Number: 4,936,843
[45] Date of Patent: Jun. 26, 1990

[54] KIRSCHNER WIRE CLAMP AND TENSIONER

[75] Inventor: Gary W. Sohngen, San Pedro, Calif.

[73] Assignee: Ace Orthopedic Manufacturing, Los Angeles, Calif.

[21] Appl. No.: 311,537

[22] Filed: Feb. 16, 1989

[51] Int. Cl.⁵ .................................................. A61F 5/00
[52] U.S. Cl. ........................................ 606/54; 606/56; 606/57
[58] Field of Search ........... 128/92 Z, 92 ZZ, 92 ZK, 128/92 ZW, 92 YF, 92 YE, 92 VL, 92 ZY, 92 VY, 92 VW; 269/322; 606/55, 56, 57, 58, 59, 60, 62, 76, 71, 82, 87, 88

[56] References Cited

U.S. PATENT DOCUMENTS

| | | | |
|---|---|---|---|
| 2,014,638 | 9/1935 | Scofield | 128/92 ZW |
| 3,709,219 | 1/1973 | Halloran | 128/92 ZZ |
| 3,977,397 | 8/1976 | Kalnberz | 128/92 Z |
| 3,985,127 | 10/1976 | Volkov | 128/92 Z |
| 4,187,841 | 2/1980 | Knutson | 128/92 ZZ |
| 4,220,146 | 9/1980 | Cloutier | 128/92 ZZ |
| 4,338,927 | 7/1982 | Volkov | 128/92 Z |
| 4,450,834 | 5/1984 | Fischer | 128/92 VL |
| 4,554,915 | 11/1985 | Brumfield | 128/92 Z |
| 4,615,338 | 10/1986 | Ilizarov | 128/92 ZY |
| 4,628,921 | 12/1986 | Rousso | 128/92 Z |
| 4,768,524 | 9/1988 | Hardy | 128/92 Z |
| 4,784,125 | 11/1988 | Monticelli | 128/92 Z |
| 4,823,781 | 4/1989 | Buchanan | 128/92 Z |

FOREIGN PATENT DOCUMENTS 0910154  3/1982  U.S.S.R. ............... 128/92 Z

Primary Examiner—Robert A. Hafer
Assistant Examiner—Michael Brown
Attorney, Agent, or Firm—Grant L. Hubbard

[57] ABSTRACT

Tensioning clamps for bone positioning wires of external fixation devices used in orthopedic surgery having clamping structure associated with tensioning guide device for being moved reciprocally therewith for clamping said bone positioning wire for movement with the tensioning guide device, and a clamp and tension indicator including annular washer springs in a cavity between compression surfaces, the distance between which is indicative of the amount of compression, is disclosed.

2 Claims, 1 Drawing Sheet

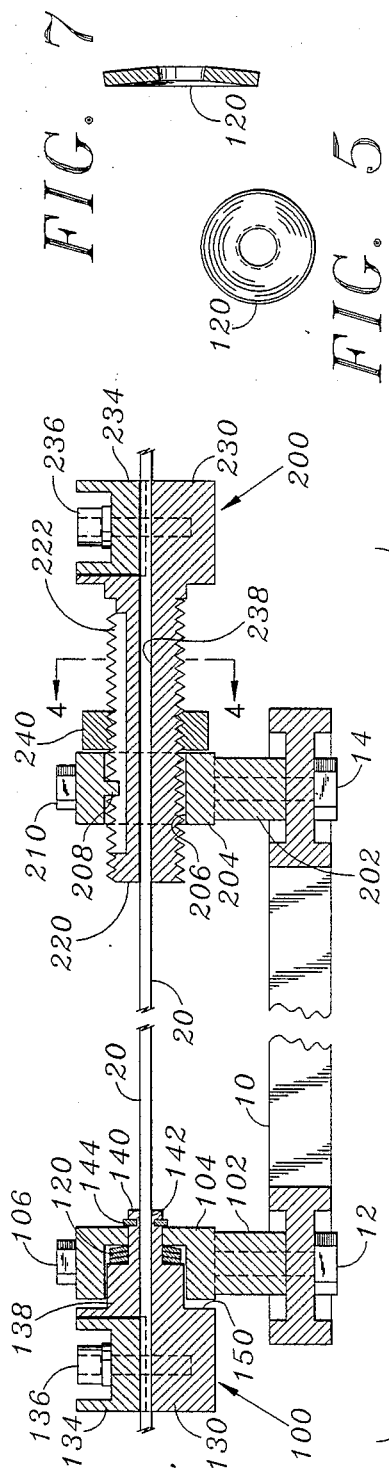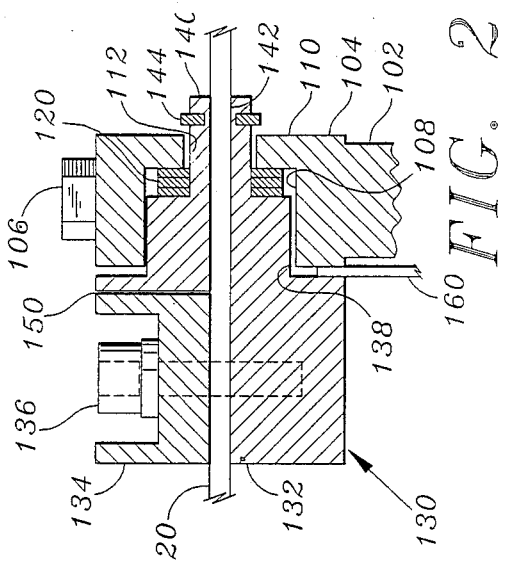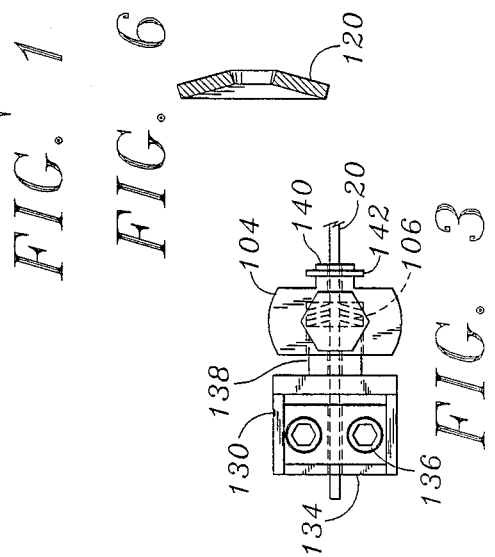

KIRSCHNER WIRE CLAMP AND TENSIONER

BACKGROUND OF THE INVENTION

The present invention relates to orthopedic surgical devices generally, and more specifically, the present invention relates to devices which utilize Kirschner wires in connection with external fixator rings or other devices for positioning bone fragments or for tensioning a bone for accelerating bone length growth.

External fixation devices have been used for many years and are well known in the surgical field and are a common appliance in the practice of orthopedic surgeons for treating trauma, especially of the leg and arm bones. The state of the art was reviewed by Brooker, Andrew F. Jr., M.D., and Edwards, Charles C., M.D., in EXTERNAL FIXATION THE CURRENT STATE OF THE ART, Williams & Wilkens, Baltimore/London 1979. Among the devices currently in use are the Ilizarov external fixator described by F. A. Ilizarov, "Compression Distraction Apparatus," U.S.S.R. Patent No. 538710-3338801 1-28-13, and in U.S. Pat. No. 4,615,338. The Ilizarov external fixator is described along with its applications in a product information bulletin published by Richards Medical Company, 1450 Brooks Road, Memphis, TN 38116. Another external fixator is the Monticelli Spinelli external fixation system marketed by Howmedica, and described in product literature distributed by the manufacturer.

An improved external fixation device was developed by Dr. David A. Fischer, and is described in his Patent No. 4,450,834. The Fischer external fixation device is distributed by Ace Orthopedic Manufacturing, Inc., of Los Angeles, CA. Many other external fixation devices are also known, but the foregoing are sufficient to exemplify the general structure and utilization of such devices.

Generally speaking, the type of fixation device which is under consideration may be described as comprising at least two, and frequently three rings or partial rings which are sized and configured to extend around the body part which is being treated for trauma or to accelerate bone length growth, most frequently in the treatment of trauma. The Fischer device typically comprises two arcuate portions which when connected together through bolts and clamps or other means, form a complete ring encircling the leg, arm, etc., under treatment. The Howmedica device, designed by Jaquet Orthopedie, also utilizes matching arcuate sections which are connected together, although the construction and operation differ considerably from the Fischer device. The Ilizarov device is of a similar construction but uses a different kind of ring construction and configuration.

The external fixation device which is the subject of this application also comprises clamps for pins which may be screwed into the bone fragments, the clamps being connected to the rings in such a manner that by movement of the clamps and the rings, or both, the bone fragments may be aligned to permit proper healing.

Another utilization of external fixation devices of the type which are the subject of this application utilizes Kirschner wires which extend through the bone, or bone fragment, and are clamped at the respective ends thereof on different portions of the ring, typically diametrical portions of the ring, and are held under very strong tension to permit bending of the wire. Kirschner wires require only a very small passage through the bone, and thus are less traumatic than the screws which are sometimes necessary.

The present invention comprises and improved Kirschner wire clamping and tensioning device. A Kirschner wire may be described simply as an elongate wire of biologically compatible metal or alloy which is relatively rigid. For convenience, reference has been made to such wires as the Kirschner wire, but any wire under tension extending through a bone or a bone fragment may be utilized in connection with the present invention.

The present invention provides a clamp for rigid tensioned wires in external fixation devices which permits tensioning to a desired and known degree, locking without loss of tensioning, and without the necessity for additional torque wrenches or other torquing devices which measure the amount of tension on the wire.

SUMMARY OF THE INVENTION

The present invention comprises complementary clamps for the respective ends of a wire, or other tensioned wire in an orthopedic external fixation device, which are secured at different, and usually generally diametric, portions of an external fixation device ring, and which coact one with another to provide clamping without bending, cutting, or otherwise distorting the tensioned wire, and which permit tensioning of the wire to a known degree without the use of external torque measuring devices.

The present invention is considered to be an improved external fixation device for use in orthopedic surgery and treatment which comprises one or more external fixation rings which, in use, surround the bone fragments or bone to be positioned or treated, bone positioning wires extending through the bone fragments or bone for exerting a force on the bone fragments or bones and tensioning means comprising first and second clamps and means securing the first and clamps generally diametrically on the rings for maintaining said wires in tension. The improvement is in the tensioning means which comprise a tensioner clamp and an indicator clamp.

The tensioner clamp, also referred to as first clamp and tensioner means, comprises ring mounting means defining an aperture therethrough, tensioning guide means comprising an elongate member defining a passage therethrough for receiving a bone positioning wire, the elongate portion extending through the aperture in the ring mounting means, tensioning means associated with the tensioning guide means for forcing longitudinal movement of the tensioning guide means relative to the ring mounting means, and clamping structure comprising associated with the tensioning guide means for being moved reciprocally therewith for clamping said bone positioning wire for moving an end of the bone positioning wire the tensioning guide means.

The indicator clamp, also called second clamp and tension indicator means, comprises second ring mounting means defining a cavity defined in part by a first compression surface and an aperture through the first compression surface, second clamping means for the bone positioning wire, compression guide means received for reciprocal movement in the cavity and defining a second compression surface spaced from and substantially parallel to the first compression surface, the compression guide means defining a passage therethrough for receiving the bone positioning wire, and at least one annular washer spring in the cavity between the compression surfaces, the bone positioning wire extending therethrough.

First and second mounting means are provided for mounting the first clamp and tensioner and the second clamp and tension indicator, respectively, on an external fixation ring in generally diametrically opposed locations, such that, in use, the bone positioning wire extends through the first clamp and tensioner and the second clamp and tension indicator and, in the second clamp and tension indicator, through at least one annular washer spring. The second clamp and tension indicator are so constructed and configured as to define a feeler gauge space between the indicator clamp body, which comprises the ring mounting means, and the second clamping means. The tensioning means is so constructed and configured as to permit tension to be applied to the bone positioning wire by the first clamp and tensioner pulling the second clamping means toward the second ring mounting mean against a predetermined bias force of one or more annular washer springs causing the feeler gauge space to become smaller as tension on the bone position wire increases. The width of the feeler gauge space is, thus, a known and predetermined function of the tension force on the bone positioning wire.

BRIEF DESCRIPTION OF THE DRAWINGS

FIG. 1 is a side view of the apparatus of this invention showing portions cutaway to depict the internal structure in cross-section.

FIG. 2 is an enlarged cross-section view of a portion of the apparatus shown at the left of FIG. 1.

FIG. 3 is a top plan view of that portion of the apparatus shown at the left in FIG. 1.

FIG. 4 is an end view, in partial cross-section, taken along lines 4—4 in the direction of the arrows in FIG. 1.

FIG. 5 is a plan view of the Belleville washer of the type which is used for measuring torque in this apparatus.

FIG. 6 is a side cross-sectional view taken along the diameter of the washer shown in FIG. 5 perpendicular to the plane as shown in FIG. 5, with the washer in the relaxed, non-compressed configuration.

FIG. 7 is a side view in cross-section corresponding to that shown in FIG. 6, but with the washer in compressed configuration.

DESCRIPTION OF THE PREFERRED EMBODIMENT

In the following discussion, reference will be made to particular structures and to particular relationships. It will be understood that a great deal of latitude is available to those skilled in the art with respect to the shapes and sizes of the components without departing from the scope of the invention, so long as the fundamental function of clamping and tensioning the orthopedic fixation wire, the wire, is accomplished in the general manner described.

Reference is made first to FIG. 1 which shows an overall assembly of the two co-operating clamps, each clamp being secured to a different portion of the external fixation ring, and positioning the fixation wire for tensioning. In FIG. 1, the ring 10 is depicted in partial cross-section. The ring 10 may be of any type but, for convenience, is shown as being of the type depicted in Fischer's U.S. Pat. No. 4,450,834. A bone positioning or stretching orthopedic wire, such as a wire, is shown at 20 in FIG. 1. One of the clamps, described as the indicator clamp, is indicated generally at 100 on the left side of the drawing in FIG. 1, and the other of the clamps of this invention, described generally as the tensioner clamp, is shown generally at 200 in the right-hand portion of the drawing. In use, the indicator clamp and the tensioner clamp are mounted generally diametrically on the ring, i.e. roughly across the ring, on a chord in the general vicinity of a diameter of the ring.

The indicator clamp, or tension indicating means, 100 comprises a tensioner body which comprises a shank portion 102 which is adapted to receive a screw 12 securing the indicator clamp to a desired position on the orthopedic fixator ring 10. The shank portion 102 supports the indicator body, which defines a compression washer receiving portion 104, and which has formed or secured on the top a regular square or hexagonal nut portion 106 which permits the indicator clamp body to be held in position while it is being secured to the ring by the bolt 12.

Continuing to refer to FIGS. 1 and 2, and to FIG. 3 as well, the indicator body defines, in the washer receiving portion 104, a washer-receiving cavity 108, the right end of which, as shown in the figures, is partially closed by a wall 110 which has formed therein an aperture 112. The left surface, as shown in the figures, of the wall 110 defines a first compression surface which, as will be discribed more specifically, resists the tension force on the wire and applies compression to one face of the washer springs.

The cavity 108 is adapted to receive, quite loosely, one or more washers known as Belleville washers, which are shown in detail in FIGS. 5, 6 and 7. The structure and function of the Belleville washer will be discussed hereinafter in connection with its utilization in this invention but, briefly, the washers resiliently resist the tension force and are flattened according to a known and predetermined formula or degree, from a normally concavo-convexo configuration by the tension force.

The clamp means 130 of the indicator clamp comprises a clamp body 132 received in and carried by the body 102, 104, 106, as previously described. The clamp body 132 has a flat upper portion against which a clamping block 134 is clamped by one or more screws 136. The body 132 and the block 134 are formed to define a generally semicircular groove therethrough which mate to receive the wire 20 and to clamp the wire very tightly, without distorting or cutting the wire.

The clamping means also comprises a compression guide means 138 which is a cylindrical extension from the main body 132 of the clamping means, the guide means being configured and constructed to be received for reciprocal movement in the cavity 108, the end thereof defining a second compression surface, opposing the first compression surface formed by the left (as shown) side of the front wall 110. The second compression surface is spaced from and substantially parallel to the first compression surface which is defined by the partial closed end 110 of the ring mounting means. An extension, in the form of a smaller cylinder 140, extends through the aperture 112 and has formed therethrough an aperture 142 adapted and configured to receive the wire 20. In the preferred embodiment, a groove is formed in the end of extension 140 to receive a keeper ring 144 to maintain the assembly 100 together.

As shown in FIG. 2 most clearly, a plurality, for example three or four or five, of Belleville washers are received about the extension 140 and in the cavity 108 between the compression surfaces defined by the wall 110 and the end of the compression guide 138.

The clamping means is so constructed and the dimensions are so defined as to provide a gap 150 between the front face of the clamping body 132 and the rear face of the indicator clamp body 102, 104, 106, 108, 110. When a predetermined tension on the kirshner wire is reached, the gap 150 will have a predetermined width, such that a feeler gauge 160 will just slide into the gap with essentially no space to spare.

In a generally diametrical relationship to the indicator clamp, or second clamp and tension indicator, just described, mounted on the ring 10, is a tensioner clamp, or first clamp and tensioner, indicated generally at 200. While these two clamping and tension-related mechanisms are generally located across from one another, either exactly on the diameter or in the general vicinity of the diameter, it is of no particular consequence whether they are on the diameter or on a chord. For convenience, the two clamping and tensioning devices, which work with one another, will be described as being generally diametrically related, with the understanding that this merely means that the two structures are located generally across a significant portion of the ring from one another.

The first clamp and tensioner comprises a body which is comprised of a shank 202, which performs essentially the same function as the shank 102 previously described, and a tension bolt receiving portion 204, which has formed therethrough a passage 206, which is preferably but not necessarily a cylindrical passage, into which, at one point, a guide pin 208 extends interiorly of the passage 206. The mounting means may also include a nut formed on or added to the mounting means indicated at 210 to permit the mounting means from turning when mounting it to the ring by means of a bolt 14. For convenience in manufacture, the guide pin 208 may be formed on the end of a bolt or pin the head of which is the nut 210, which is screwed or moved into place, or a shaft having a head shown at 210 which is mounted in place, with the guide pin extending into the passageway 206 and then welded or otherwise affixed there. The manner of manufacture is, of course, secondary to the ultimate structure insofar as this invention is concerned.

A tensioning guide bolt 220, which is shown as being threaded, defines a guide groove 222 along one side thereof. As shown in FIG. 1, the guide groove 222 is in the top of the guide bolt 220. Secured to or formed integrally with the guide bolt 220 is a clamp body 230 to which a clamping block 234 is secured in clamping relationship by bolts 236. The body 230 and the clamping block 234 have formed therein generally semicircular cross-sectionally configured grooves which are aligned with a passage 238 which extends through the bolt 220. The passage 238 is adapted to receive the wire 20, and the grooves in the body 230 and the clamp block 234 are such as to receive and to permit very firm clamping, without distortion or cutting, of the wire 20. A nut 240 is threadably received on the bolt 220 and acts as the means for moving the bolt 220 to create tensioning forces.

The mode of operation of the device can now be easily be understood. As the device is assembled, with the pin extending through the patient's bone and the ring surrounding the bone, the first clamp and tensioner are clamped on one side of the ring, and the second clamp and tension indicator are clamped on the other side of the ring. The wire is extended through the apertures 142 and 238 in the first and second clamps, and the wire is clamped very securely at or approximate the respective ends thereof by the respective clamping structures, 130, 132, 134, and 136, and 230, 232, 234, and 236, just described, with the tensioner in the most relaxed, non-tensioned position, i.e. with the nut 240 near the extreme right of the bolt, as shown in FIG. 1, right-hand portion.

Once the first and second clamp structures are located on the ring and secured thereto by bolts 12 and 14, the apertures and grooves in the clamping structures aligned with the axis of the wire, and the wire is clamped therein, the orientation being such that the wire will not be bent, the tension can be applied. At this time, the Belleville washers 120 are in the cavity 108 between the first and second compression surfaces in relaxed or noncompressed configuration shown in FIGS. 3 and 6.

Tension is applied by turning the nut 240 on the bolt 220, forcing the bolt to the right, as shown in FIG. 1, thus applying tension to the wire 20. As tension is applied to the wire 20, the Belleville washer, or a plurality of such washers, in the cavity 108 are gradually compressed. As the washers are compressed, the space 150 becomes smaller and smaller. The feeler gauge 160 is either maintained in the gap or space 150 or is periodically inserted therein. Once the space 150 has reached the dimension that the feeler gauge 160 will slip very snugly thereinto, it is known from previous calculations that a predetermined tension on the wire 20 has been achieved. All this is achieved without the need of auxiliary tension measuring devices or complex torque wrenches, etc.

Belleville washers of different sizes and thicknesses are available. In a convenient embodiment of the invention, five Belleville washers, each of which is compressed from its relaxed position to its fully compressed position by the application of 55 lbs. of compression force, are placed in the cavity, and when the wire is placed under tension, the compression is applied to these rings. The compressive force necessary to fully compress five Belleville rings is simply additive, requiring a compressive force of 275 lbs., or about 130 kg. This compressive force resulting from the combined resistance to compression of the five, in this example, Belleville rings requires that a tension of 130 kg. be applied to the wire in order to close the distance between the two surfaces forming the gap 150 to the point where the feeler gauge, e.g. a gauge of 0.008 inch, will snugly be received.

Thus, when the feeler gauge is snugly received in the gap, it is known, by reason of the previously calculated forces required to compress one or a plurality of Belleville washers, quite accurately what the tension on the wire is. By adjusting the number of washers and the thickness of the feeler gauge, tensions in any desired increment may be achieved. In practice, however, it is usually necessary only to provide one set of Belleville washers, one feeler gauge, and one wire, since for a given wire the optimum tension is known or can be readily determined by simple experiment.

Once the entire apparatus has been positioned and the tension applied, the ends of the wires may be bent over or cut off.

One of the very significant factors of this invention which is of particular note is that fact that rather precise measurement and achievement of predetermined tension on the wire is possible without the need for complex and expensive torque wrenches, which become quite cumbersome in the operating room, or other tension measuring devices. Indeed, nothing beyond the conventional wrenches for tightening the bolts and a simple feeler gauge are required.

Another very advantageous and unique feature of this invention is the formation of a pair of clamping means which have a clamping body and a clamping block, each of which has mating grooves of semicircular cross-section which grip the wire very firmly without cutting the wire or weakening it. In the prior art devices for using wires, there was always a significant risk of breaking the wire as it was placed under tension, because the wire had been deformed, distorted, or weakened by the clamping or attaching mechanisms. This serious disadvantage of the prior art has been avoided in the present invention.

Furthermore, in the prior art devices, once the entire assembly has been completed and the torque applied, there is a likelihood that through distortion, slight shifts, or otherwise, the torque will be reduced. In such instances, it is necessary to relocate the torque wrench, or torque measuring device, and recheck and retorque the entire system. In the present invention, a feeler gauge, about the size of a human finger, but of desired thickness, e.g. 0.008 inch, may be used to recheck the torque at any point in time, and retorquing is accomplished using a standard wrench.

The apparatus as described is made of a corrosion-resistant material of adequate strength and hardness to permit clamping of the wire, which is typically a nitrogen-strengthened stainless steel wire. The apparatus is most advantageously made of titanium, but it could be made of stainless steel or any other suitably hard, corrosion resistant metal.

The apparatus finds its most frequent use in trauma surgery where it is used to assist in the positioning of bones for casting and/or for healing. Another very important use of the invention is in bone lengthening tensioning devices where the long bones are placed under tension adjacent the joints at the respective ends thereof to induce lengthening of the bone during growth.

INDUSTRIAL APPLICATION

This invention finds application in orthopedic surgery and in veterinary surgery.

What is claimed is:

1. In an external fixation device for use in orthopedic surgery and treatment which comprises one or more external fixation rings which, in use, surround the bore fragments or bone to be positioned or treated, bone positioning wires extending through the bone fragments or bone for exerting a force on the bone fragments or bones and tensioning means comprising first and second clamps and means securing the first and clamps generally diametrically on the rings for maintaining said wires in tension, the improvement wherein the tensioning means comprises:
    (a) a first clamp and tensioner comprising (i) a first body (202, 204) defining a passage therethrough, (ii) tensioning guide means (220, 222) comprising an elongate member defining an aperture (238) therethrough for receiving a bone positioning wire (20), the elongate portion extending through the passage in the first body, (iii) tension applying means (240) associated with the tensioning guide means for forcing longitudinal movement of the tensioning guide means relative to the first body, and (iv) clamping structure (230, 234, 236) associated with the tensioning guide means for being moved reciprocally therewith for clamping said bone positioning wire for movement with the tensioning guide means;
    (b) a second clamp and tension indicator comprising (i) second body (102, 104) defining a cavity (108) which is defined in part by a first compression surface, and an aperture through the second body, (ii) second clamping means (130, 134, 136) for the bone positioning wire, (iii) compression guide means (138) received for reciprocal movement in the cavity (108) and defining a second compression surface spaced from and substantially parallel to the first compression surface, the compression guide means defining a passage (142) therethrough for receiving the bone positioning wire, and (iv) at least one annular washer spring (120) in the cavity between the compression surfaces, the annular washer spring receiving the bone positioning wire (20) therethrough; and
    (c) first and second mounting means (12, 14) for mounting the first clamp and tensioner and the second clamp and tension indicator, respectively, on an external fixation ring (10) in generally diametrically opposed locations;
    the bone positioning wire extending, in use, through the first clamp and tensioner and the second clamp and tension indicator, the second clamp and tension indicator being so constructed and configured as to define a feeler gauge space between the second body and the second clamping means, the tensioning means being so constructed and configured as to permit tension to be applied to the bone position wire by the first clamp and tensioner, such tension pulling the second clamping means toward the second block against a predetermined bias force of one or more annular washer springs causing the feeler gauge space to become smaller as tension on the bone position wire increases, the width of the feeler gauge space thus being a known and predetermined function of the tension force on the bone positioning wire.

2. In an external fixation device for use in orthopedic surgery and treatment which comprises one or more external fixation rings which, in use, surround the bone fragments or bone to be positioned or treated, bone positioning wires extending through the bone fragments or bone for exerting a force on the bone fragments or bones and tensioning means comprising first and second clamps and means securing the first and clamps generally diametrically on the rings for maintaining said wires in tension, the improvement wherein the tensioning means comprises:
    (a) a tensioner comprising a first body, first means for clamping the bone positioning wire proximate a first end thereof, and means moving the first means for clamping the bone positioning wire relative to the body to thereby move the first end of the wire relative to the body; and
    (b) an indicator comprising a second body, second means for clamping the bone positioning wire proximate a second end thereof, and annular spring means disposed around the bone positioning wire and between the second body and the second means for clamping, said spring means being so constructed as to be resiliently compressed between the second body and the second means for clamping by tension applied on the positioning wire, the second body and second clamping means being so constructed and disposed relative to each other that upon compression of the spring means a portions of the second body and second clamping means, respectively, are moved closer to one another, the space between said portions being a known function of the compression of the spring means and hence of the tension on the bore positioning wire.

* * * * *